United States Patent [19]

Gates et al.

[11] Patent Number: 5,024,693
[45] Date of Patent: Jun. 18, 1991

[54] HERBICIDES

[75] Inventors: Peter S. Gates, Fulbourn; Graham P. Jones, Sawston, both of England

[73] Assignee: Schering Agrochemicals Ltd., England

[21] Appl. No.: 416,153

[22] Filed: Oct. 2, 1989

[30] Foreign Application Priority Data

Oct. 4, 1988 [GB] United Kingdom ............... 8823288

[51] Int. Cl.$^5$ ............... A01N 43/54; C07D 401/12; C07D 239/34; C07D 239/52
[52] U.S. Cl. ............................... 71/92; 71/90; 71/93; 544/300; 544/301; 544/310; 544/311; 544/316; 544/317; 544/296; 544/284; 544/263; 544/219; 544/262; 544/281; 544/312
[58] Field of Search ............ 71/92, 90, 93; 544/300, 544/301, 310, 311, 316, 317, 296, 284, 263, 219, 262, 281, 312

[56] References Cited

U.S. PATENT DOCUMENTS

| 4,797,146 | 1/1989 | Sasse et al. | 544/316 |
| 4,871,387 | 10/1989 | Sasse et al. | 544/316 |
| 4,931,560 | 6/1990 | Hubele | 544/316 |
| 4,980,355 | 12/1990 | Zondler et al. | 544/316 |

Primary Examiner—John M. Ford
Attorney, Agent, or Firm—Ostrolenk, Faber, Gerb & Soffen

[57] ABSTRACT

The invention provides novel herbicidal sulphonanilides of the formula:

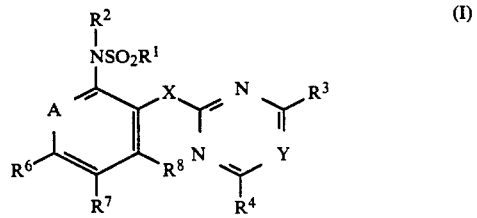

where $R^1$-$R^8$ have the meanings given in the specification, and salts thereof, processes for their preparation, and herbicidal compositions containing them.

20 Claims, No Drawings

HERBICIDES

This invention concerns herbicidal sulphonanilides, processes for their preparation, and compositions containing them.

In one aspect, the invention provides novel sulphonanilides of the formula:

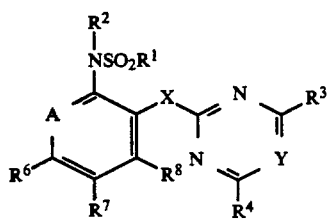

and salts thereof, where:
A is nitrogen or a group $CR^5$;
X is oxygen or sulphur;
Y is nitrogen or a group $CR^9$;
$R^1$ is an optionally-substituted alkyl, alkenyl, alkynyl, cycloalkyl, aryl, heterocyclyl, benzoheterocyclyl or amino group;
$R^2$ is hydrogen, an optionally-substituted alkyl or carboxylic acyl group, or a group $-SO_2R^1$;
$R^3$ and $R^4$, which may be the same or different, are each hydrogen, halo, an optionally-substituted alkyl, alkoxy, cycloalkyl or amino group, or a heterocyclyl group;
$R^6$, $R^7$ and $R^8$, which may be the same or different, are each hydrogen, halo, cyano, a group $COOR^{10}$, or an optionally-substituted alkyl, alkoxy or amino group;
$R^5$ is a group as defined above for $R^6$, $R^7$ and $R^8$, or is an optionally-substituted aryloxy or heterocyclyloxy group; and
$R^9$ and $R^{10}$ each represent hydrogen or an optionally-substituted alkyl group.

When any of groups $R^1$ to $R^{10}$ is or contains an alkyl group, that group is preferably of 1 to 6 carbon atoms, especially of 1 to 4 carbon atoms, for example methyl, ethyl, n-propyl, isopropyl, n-butyl or t-butyl. The group may be unsubstituted, or substituted for example by one or more halogen atoms, carboxy groups, cyano groups or alkoxycarbonyl groups of 1 to 4 carbon atoms, specific preferred substituted groups being chloromethyl, fluoromethyl, cyanomethyl, carboxymethyl, trifluoromethyl, methoxycarbonylmethyl and ethoxycarbonylmethyl.

When $R^1$ represents alkenyl or alkynyl, it is preferably of 2 to 6 carbon atoms, for example vinyl, allyl or propargyl.

When $R^1$ represents a cycloalkyl group, it is preferably of 3 to 7, especially of 5 or 6 carbon atoms, especially a cyclopentyl or cyclohexyl group.

When $R^1$ represents an aryl group, it is preferably a phenyl group, which is desirably substituted by one or more alkyl, alkoxy, alkoxycarbonyl or alkylthio groups of 1 to 4 carbon atoms (which may themselves be further substituted), halogen atoms, cyano groups, aminosulphonyl groups or nitro groups, especially a phenyl group substituted by one or more chlorine, bromine or fluorine atoms, and/or one or more methyl, methoxy, trifluoromethyl, methylthio, methoxycarbonyl, ethoxycarbonyl or nitro groups.

When $R^1$, $R^3$ or $R^4$ represents a heterocyclyl group, that group is preferably a nitrogen-containing heterocycle, for example a 5- or 6-membered single ring heterocycle, e.g. pyrrolyl, pyrimidinyl, 1-triazolyl or 1-imidazolyl. $R^1$ may also with advantage represent pyridyl, furyl, 2-thienyl, or a bicyclic heterocyclyl group, e.g. a thiazolotriazolyl, triazolopyrimidinyl or pyrazolopyrimidinyl group.

When $R^1$ represents a benzoheterocyclyl group, it is preferably a benzthiophene, benzodioxole, quinoline, quinazoline, benzothiazole or dihydrobenzofuran group.

When $R^1$ or any $R^3$ to $R^8$ represents a substituted amino group, it may be mono- or di-substituted, for example by alkyl of 1 to 4 carbon atoms, alkenyl of 2 to 4 carbon atoms, carbamoyl, or carboxylic acyl, alkoxycarbonyl, alkylcarbamoyl or dialkylcarbamoyl in which any alkyl group is of 1 to 4 carbon atoms.

When $R^3$ or $R^4$ represents cycloalkyl, it is preferably cyclopropyl.

When $R^5$ represents a heterocyclyloxy group, it is preferably a pyrimidyloxy or triazinyloxy group.

X preferably represents oxygen.

Specific preferred groups which $R^1$ may represent include methyl, chloromethyl, cyanomethyl, trifluoromethyl, 2-chlorophenyl, methoxycarbonylamino or thiazolotriazolyl.

$R^2$ preferably represents hydrogen.

$R^3$ and $R^4$ are each desirably hydrogen, methyl, methoxy or chloro. It is particularly preferred for $R^3$ and $R^4$ to be identical, and especially for both to be methoxy.

$R^5$ preferably represents hydrogen, halo (especially fluoro, chloro or bromo), methyl or trifluoromethyl.

$R^6$, $R^7$ and $R^8$ each preferably represent hydrogen, methyl or chloro. It is particularly preferred for all three to represent hydrogen.

The salts of the compounds of formula I are preferably those formed with strong bases such as alkali-metal (e.g. potassium or sodium) salts and amine salts (e.g. triethylamine, di-isopropylamine, cyclohexylamine or piperidine salts).

Particularly preferred compounds according to the invention are those of the Examples provided hereinafter. Particular mention may be made, however, of 2'-chloro-6'-(4,6-dimethoxy-2-pyrimidinyloxy)-1,1,1-trifluoromethanesulphonanilide and the salts thereof.

In another aspect, the invention provides a process for the preparation of a sulphonanilide of formula I in which a corresponding aniline of the formula:

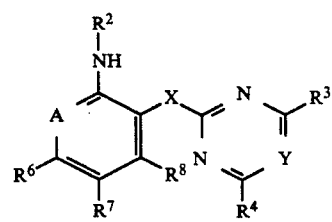

where A, X, Y and $R^3$ to $R^8$ are as defined hereinbefore is reacted with a suitable sulphonic anhydride of the formula $(R^1SO_2)_2O$ or sulphonyl halide of the formula $R^1SO_2Hal$, where Hal is a halogen atom, to give the desired compound.

The reaction is desirably effected in the presence of a base, for example an organic base such as pyridine.

The compounds of formula II may themselves be prepared by a process in which a substituted aniline of the formula:

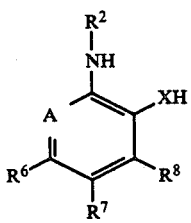

(III)

where X, $R^2$ and $R^6$ to $R^8$ are as defined hereinbefore, is reacted in the presence of a base with a compound of the formula:

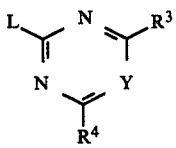

(IV)

where Y, $R^3$ and $R^4$ are as defined hereinbefore, and L is a leaving group, to give the desired compound.

The leaving group L may be any suitable such group, but is preferably a halogen atom, especially a chlorine atom, or a methylsulphonyl group.

The base employed is preferably an alkali-metal base, e.g. potassium t-butoxide or potassium carbonate, and the reaction is desirably effected in a suitable solvent medium, e.g. dimethylformamide or a ketone, e.g. methyl ethyl ketone.

The salts of the compounds of formula I may be prepared by methods known per se from the corresponding free compounds by subjecting them to the action of a suitable base in a suitable solvent (e.g. an ether).

The compounds of formula I in which $R^2$ is other than hydrogen may alternatively be prepared from the salts of the compounds of formula I by reaction thereof in a manner known per se with a suitable alkylating or carboxylating agent containing the desired group $R^2$.

The compounds of formula I are herbicidally-active against a wide range of broad-leaved and grassy weeds, but are comparatively safe to certain crop species. They may thus be of use as selective herbicides, particularly in the control of a range of weeds in cereals, sugar beet or other crops, e.g. wheat, barley, maize, soya beans, oilseed rape, cotton or rice.

Desirable rates of application of the compounds of formula I or their salts range from 0.001 to 2 kg/ha, particularly from 0.005 to 1.0 kg/ha, and especially from 0.01 to 0.5 kg/ha.

In another aspect, the invention provides a composition which comprises one or more compounds of the invention in association with a suitable carrier and/or surface active agent.

The compositions usually contain from 0.01 to 99% by weight of the present compounds, and are normally produced initially as concentrates containing from 0.5 to 99%, preferably from 0.5 to 85%, and especially from 10 to 50% by weight thereof. Such concentrates are diluted if necessary before application to the locus to be treated such that the active ingredient comprises from 0.01 to 5% by weight of the formulation applied.

The carrier may be water, in which case an organic solvent may also be present, though this is not usually employed. A flowable suspension concentrate may be formed by grinding the compound with water, a wetting agent and a suspending agent, e.g. xanthan gum.

The carrier may alternatively be a water immiscible organic solvent, e.g. a hydrocarbon which boils within the range 130–270° C., e.g. xylene, in which the compound is dissolved or suspended. An emulsifiable concentrate containing a water immiscible solvent may be formed with a surface active agent so that the concentrate acts as a self-emulsifiable oil on admixture with water.

The carrier may alternatively be a water-miscible organic solvent e.g. 2-methoxy ethanol, methanol, propylene glycol, diethylene glycol, diethylene glycol monoethyl ether, methylformamide or dimethylformamide.

The carrier may alternatively be a solid, which may be finely divided or granular. Examples of suitable solids are limestone, clays, sand, mica, chalk, attapulgite, diatomite, perlite, sepiolite, silicas, silicates, lignosulphonates and solid fertilizers. The carrier can be of natural or synthetic origin or can be modified natural material.

Wettable powders soluble or dispersible in water may be formed by admixing the compound in particulate form with a particulate carrier or spraying molten compound on to the particulate carrier, admixing a wetting agent and a dispersing agent and finely grinding the whole powder mixture.

An aerosol composition may be formed by admixing the compound with a propellant, e.g. a polyhalogenated alkane such as dichlorofluoromethane, and suitably also with a solvent.

The term 'surface active agent' is used in the broad sense to include materials variously called emulsifying agents, dispersing agents and wetting agents. Such agents are well known in the art.

The surface active agents used may comprise anionic surface active agents, for example mono- or di-esters of phosphoric acid with a fatty alcohol ethoxylate, or salts of such esters, fatty alcohol sulphates such as sodium dodecyl sulphate, ethoxylated fatty alcohol sulphates, ethoxylated alkylphenol sulphates, lignin sulphates, petroleum sulphonates, alkylaryl sulphonates such as alkyl-benzene sulphonates or lower alkylnaphthalene sulphonates, salts of sulphonated naphthaleneformaldehyde condensates, salts of sulphonated phenolformaldehyde condensates, or more complex sulphonates such as the amide sulphonates, e.g. the sulphonated condensation product of oleic acid and N-methyl taurine or the dialkyl sulphosuccinates e.g. the sodium sulphonate of dioctyl succinate.

The surface active agents may also comprise non-ionic agents, for example condensation products or fatty acid esters, fatty alcohols, fatty acid amides or alkyl-substituted phenols with ethylene oxide, fatty esters of polyhydric alcohol ethers e.g. sorbitan fatty acid esters, condensation products of such esters with ethylene oxide e.g. polyoxyethylene sorbitan fatty acid esters, block copolymers of ethylene oxide and propylene oxide, acetylenic glycols such as 2,4,7,9-tetramethyl-5-decyn-4,7-diol, or ethoxylated acetylenic glycols.

The surface active agents may also comprise cationic agents, for example alkyl- and/or aryl-substituted quaternary ammonium compounds such as cetyl trimethylammonium bromide, or ethoxylated tertiary fatty amines.

Preferred surface active agents include ethoxylated fatty alcohol sulphates, lignin sulphonates, alkyl-aryl sulphonates, salts of sulphonated naphthaleneformaldehyde condensates, salts of sulphonated phenolformaldehyde condensates, sodium oleoyl N-methyltauride, dialkyl sulphosuccinates, alkyl phenol ethoxylates, and fatty alkyl ethoxylates.

The present active compounds, especially those of the Examples provided hereinafter may be admixed with another pesticide, e.g. a herbicide, fungicide or insecticide, or a plant growth regulator, particularly another herbicide. Suitable further herbicides include trietazine, linuron, MCPA, dichlorprop, isoxaben, diflufenican, metolachlor, fluometuron, oxyfluorfen, fomesafen, bentazone, prometryne, norflurazon, chlomazone, EPTC, imazaquin, more especially isoproturon, methabenzthiazuron, trifluralin, ioxynil, bromoxynil, benazolin, mecoprop, fluroxypyr, alachlor, acifluorfen, lactofen, metribuzin and pendimethalin, and most particularly ethofumesate and phenmedipham.

The present compounds may be applied to plants, the soil, land or aquatic areas, and particularly to a locus at which a crop is growing or is about to grow. The compounds are active both pre- and post-emergence.

The invention is illustrated by the following Examples, in which Me=methyl, Et=ethyl, Ph=phenyl, cyPr=cyclopropyl and cyhex=cyclohexyl.

EXAMPLE 1

2'-Chloro-6'-(4,6-dimethoxy-2-pyrimidinyloxy)-1,1,1-trifluoromethanesulphonanilide (a) 2-Chloro-6-(4,6-dimethoxy-2-pyrimidinyloxy)aniline Potassium t-butoxide (22.4 g) was added portionwise to stirred, cooled 2-chloro-6-hydroxyaniline hydrobromide (22.5 g) in dimethylformamide (100 ml) under nitrogen. After 10 minutes, 4,6-dimethoxy-2-methylsulphonyl pyrimidine (21.8 g) was added, and the mixture was heated at 80° C. with stirring for 22 hours. After addition to ice/water, the precipitated solid was separated by filtration, washed thoroughly with water, dried and recrystallised from isopropanol yielding 17.5 g of the desired product, mp 84°–86° C. Reduction in volume of the mother liquors gave a further 0.85 g of product, mp 86°–87° C.

(b) 2'-Chloro-6'-(4,6-dimethoxy-2-pyrimidinyloxy)-1,1,1-trifluoromethanesulphonanilide potassium salt Trifluoromethanesulphonic anhydride (3.4 g) in dichloromethane (5 ml) was added dropwise with stirring and ice cooling to the product of stage (a) (3.4 g) and pyridine (1.0 g) in dichloromethane (25 ml). After 6 hours stirring at room temperature, the dichloromethane solution was washed with water, dilute hydrochloric acid and water again, dried over magnesium sulphate and run down under vacuum. The residue was stirred with dilute sodium hydroxide solution (0.7 g sodium hydroxide in 30 ml water) and ether for about 15 minutes. The aqueous solution was separated, washed with ether and then taken to pH=3 by addition of hydrochloric acid followed by a little sodium bicarbonate. The precipitated orange solid was filtered off and dried to yield 2.4 g of crude product, mp 141°–143° C. This solid was taken up in ether and the solution was stirred vigorously with a solution of potassium bicarbonate (2.0 g) in water (30 ml). The precipitated potassium salt was filtered off and washed with ether to give 1.7 g of product.

(c) 2'-Chloro-6'-(4,6-dimethoxy-2-pyrimidinyloxy)-1,1,1-trifluoromethanesulphonanilide To regenerate the free title product from the potassium salt of stage (b), the salt was stirred with ether (30 ml) and water (30 ml). Hydrochloric acid was added to pH=3. The ether solution was separated, washed with water, dried over magnesium sulphate, and run down. The residue was washed with petroleum ether (bp 40°–60° C.) and dried giving 1.4 g of pure product, mp 147°–149° C.

EXAMPLE 2

2'-Chloro-6'-(4,6-dimethoxy-2-pyrimidinyloxy)methanesulphonanilide

Methanesulphonyl chloride (0.8 g) was added dropwise with stirring and ice cooling to the product of Example 1 stage (a) in pyridine (10 ml) containing 0.1 g of 4-dimethylaminopyridine as catalyst. The mixture was stirred for 4 hours at room temperature and allowed to stand overnight. Addition to a mixture of ice, water and ether with stirring, acidification to pH=4, separation and work up of the ethereal layer gave 2.5 g of crude product as an orange glass. The glass was redissolved in ether and stirred with aqueous sodium hydroxide (0.3 g NaOH in 30 ml water). The mixture was stirred until the ether had evaporated and the precipitated solid was filtered off. The aqueous solution was acidified, and the crude title product filtered off and washed with water and a little ether giving 0.8 g, mp 140°–142° C. Recrystallisation from isopropanol gave 0.6 g, mp 147°–148° C.

EXAMPLES 3–37

The following compounds of formula I in which X represents oxygen, Y represents —CH= and $R^2$, $R^6$, $R^7$ and $R^8$ all represent hydrogen were prepared by methods analogous to those of Examples 1 and 2:

| Ex | A | $R^1$ | $R^3$ | $R^4$ | mp (°C.) |
|---|---|---|---|---|---|
| 3 | C—H | Me | OMe | OMe | 145–146 |
| 4 | C—H | CF$_3$ | OMe | OMe | 102–103 |
| 5 | C—H | CH$_2$CN | OMe | OMe | 121–123 |
| 6 | C—H | CH$_2$Ph | OMe | OMe | 149–151 |
| 7 | C—H | Ph | OMe | OMe | 125–126 |
| 8 | C—H | 2-ClPh | OMe | OMe | 142–143 |
| 9 | C—H | 4-ClPh | OMe | OMe | 127–128 |
| 10 | C—H | 2-COOMePh | OMe | OMe | 151–152 |
| 11 | C—H | Thiazolo[3,2-b][1,2,4]triazol-2-yl | OMe | OMe | 152–154 |
| 12 | C—H | 5,7-Dimethyl[1,2,4]triazolo[1,5-a]pyrimidin-2-yl | OMe | OMe | 161–163 |
| 13 | C—H | 5-Me-3-COOMe-pyrazolo[1,5-a]pyrimidin-2-yl | OMe | OMe | 223–225 |
| 14 | C—Me | CF$_3$ | OMe | OMe | 155–156 |
| 15 | C—Cl | Me | H | H | 222–224 |
| 16 | C—Cl | Me | OMe | Cl | 137–139 |
| 17 | C—Cl | CH$_2$CN | OMe | OMe | 133–134 |
| 18 | C—Cl | CF$_3$ | H | H | 143–146 |
| 19 | C—Cl | CF$_3$ | Me | Me | 206–209 |
| 20 | C—Cl | CF$_3$ | OMe | Cl | 163–165 |
| 21 | C—Cl | CF$_3$ | OMe | cyPr | 139–140 |
| 22 | C—Cl | NHCOOMe | Me | Me | 136–137 |
| 23 | C—Cl | NHCOOMe | OMe | OMe | 50–60 |
| 24 | C—Cl | Thiazolo[3,2-b][1,2,4]triazol-2-yl | H | H | 229–232 |
| 25 | C—Cl | Thiazolo[3,2-b] | OMe | OMe | 113–115 |

-continued

| Ex | A | R$^1$ | R$^3$ | R$^4$ | mp (°C.) |
|---|---|---|---|---|---|
| | | [1,2,4]triazol-2-yl | | | |
| 26 | C—Br | CF$_3$ | OMe | OMe | 46–49 |
| 27 | C—F | Me | OMe | OMe | 106–108 |
| 28 | C—F | Me | OMe | Me | 180–181 |
| 29 | C—F | CH$_2$CN | OMe | OMe | 133–135 |
| 30 | C—Cl | CH$_2$Cl | OMe | OMe | 125–126 |
| 31 | C—F | 1-CNEt | OMe | OMe | 56–58 |
| 32 | C—F | CF$_3$ | OMe | OMe | 151–153 |
| 33 | C—F | CF$_3$ | OMe | Me | 190–192 |
| 34 | C—CF$_3$ | CF$_3$ | OMe | OMe | 139–141 |
| 35 | —N= | CF$_3$ | OMe | OMe | 145–150 |
| 36 | —N= | Me | OMe | OMe | 184–188 |
| 37 | —N= | 2-ClPh | OMe | OMe | 154–156 |

EXAMPLES 38–51

The following compounds of formula I in which R$^2$ and R$^7$ both represent hydrogen, and R$^3$ and R$^4$ both represent methoxy were prepared by methods analogous to those of Examples 1 and 2:

| Ex | A | R$^1$ | R$^6$ | R$^8$ | X | Y | mp (°C.) |
|---|---|---|---|---|---|---|---|
| 38 | C—H | Me | H | H | S | =CH— | 115–117 |
| 39 | C—H | CH$_2$CN | H | H | S | =CH— | 116–118 |
| 40 | C—H | CH$_2$Ph | H | H | S | =CH— | 130–131 |
| 41 | C—H | CF$_3$ | H | H | S | =CH— | 107–108 |
| 42 | C—H | CF$_3$ | Cl | H | O | =CH— | 107–108 |
| 43 | C—H | CF$_3$ | Me | H | O | =CH— | 110–111 |
| 44 | C—H | 5,7-DiMe-[1,2,4]triazolo[1,5-a]pyrimidin-2-yl | H | H | S | =CH— | 90–93 |
| 45 | C—Me | CF$_3$ | H | Me | O | =CH— | 147–149 |
| 46 | C—Me | Me | H | Me | O | =CH— | 134–135 |
| 47 | C—F | CF$_3$ | H | Me | O | =CH— | 153–155 |
| 48 | C—F | Me | H | Me | O | =CH— | 138–140 |
| 49 | C—Cl | Me | H | H | O | =N— | 145–147 |
| 50 | C—Cl | CF$_3$ | H | H | S | =CH— | 133–135 |
| 51 | C—Cl | CF$_3$ | H | H | O | =N— | 175–176 |

EXAMPLE 52

N-Acetyl-2'-chloro-6'-(4,6-dimethyl-2-pyrimidinyloxy)-thiazolo [3,2-b][1,2,4]triazole-2-sulphonamide Sodium hydride (80% in oil, 0.29 g) was washed by decantation with petrol, and was added as a slurry in tetrahydrofuran to 2'-chloro-6'-(4,6-dimethyl-2-pyrimidinyloxy) acetanilide (2.7 g) in tetrahydrofuran (30 ml) with stirring and cooling, and was stirred for a further 70 minutes. Thiazolo[3,2-b][1,2,4]-triazole-2-sulphonyl chloride (1.03 g) was then added at 15° C., and the mixture was stirred for 24 hours, after which it was run down and stirred with sodium hydroxide (0.3 g) in water/ether for 3 hours. The mixture was then filtered, and the solid product was washed with water and ether. It was then successively recrystallised from ethanol/acetone with volume reduction and, after filtration, from acetonitrile to give the desired product (0.6 g), mp 190°–192° C.

EXAMPLE 53

2'-Chloro-6'-(4,6-dimethoxy-2-pyrimidinyloxy)-1,1,1-trifluoromethanesulphonanilide triethylamine salt Triethylamine (0.4 g) in diethyl ether (10 ml) was added dropwise to a stirred, cooled solution of the product of Example 1(c) (1.5 g) in diethyl ether (40 ml), and the mixture was stirred for 30 minutes, then filtered to give 1.6 g of the desired product as a white solid.

EXAMPLES 54–59

The following salts were prepared by methods analogous to that of Example 53:

54. Sodium salt of compd of Ex 1(c), mp ≧350° C.,
55. Triethylamine salt of compd of Ex 1(c), mp 121°–2° C.,
56. Di-isopropylamine salt of Ex 1(c), mp 148°–9° C.,
57. Piperidine salt of compd of Ex 1(c), mp 162°–3° C.,
58. Cyclohexylamine salt of compd of Ex 1(c), mp 165°–6° C.,
59. Potassium salt of compd of Ex 32.

EXAMPLE 60

2'-Chloro-6'-(4,6-dimethoxy-2-pyrimidinyloxy)-N-methyl-1,1,1-trifluoromethanesulphonanilide Methyl iodide (0.64 g) was added with stirring to a solution of the product of Example 1(b) (1.8 g) in dimethylformamide (10 ml), and stirring was continued for 30 minutes. The mixture was allowed to stand overnight, and was then added to ice/water and extracted into diethyl ether. The extract was washed with water three times, dried and run down to give the desired product as a yellow glass (1.4 g). On recrystallisation from 80–100 petroleum ether, this gave 0.95 g of product, mp 102°–103° C.

HERBICIDAL EXAMPLE A (Pre-Emergence)

Seeds of the weed species listed below were sown in anodised aluminium pans 19 cm long×9.5 cm wide×6 cm deep, containing sterilized sandy loam. They were watered and then sprayed with the compounds of the Examples listed below formulated as a solution/suspension in 1:1 by volume of acetone and the wetting agent polyoxyethylene (20 mols) monolaurate solution (2 g per liter).

The concentration of each test compound and volume of application were calculated to give the desired rate of application of the compound in 450 liters per hectare. After 3 to 4 weeks growth in the controlled environment room (20° C.; 75–95% relative humidity; 14 hours per day artificial illumination) the plants were visually assessed for any herbicidal response.

All differences from an untreated control were scored accordingly to an index where 0=no effect, 1=1–24% effect, 2=25–69% effect, 3=70–89% effect and 4=90–100% effect. In the table below, the following letters are used to denote the plant species:

a - *Polygonum lapathifolium* (Pale persicaria)
b - *Galium aparine* (cleavers)
c - *Chrysanthemum segetum* (corn marigold)
d - *Alopecurus myosuroides* (blackgrass)
e - *Agropyron repens* (Couchgrass)
f - *Avena fatua* (wild oat)
g - *Abutilon theophrasti* (velvetleaf)
h - *Cyperus esculentus* (yellow nutsedge)
i - *Pharbitis purpurea* (morningglory)
j - *Echinochloa crus-galli* (barnyardgrass)
k - *Setaria viridis* (green foxtail)
l - *Solanum nigrum* (black nightshade)

The results obtained were as follows:

| Ex | Kg/ha | a | b | c | d | e | f | g | h | i | j | k | l |
|---|---|---|---|---|---|---|---|---|---|---|---|---|---|
| 1 | 0.25 | 2 | 4 | 4 | 1 | 0 | 0 | 2 | 2 | 2 | 0 | 0 | — |

-continued

| Ex | Kg/ha | a | b | c | d | e | f | g | h | i | j | k | l |
|----|-------|---|---|---|---|---|---|---|---|---|---|---|---|
| 11 | 1.0   | 2 | 2 | 4 | 2 | 2 | 2 | 2 | 0 | 0 | 2 | 0 | — |
| 25 | 1.0   | 4 | 4 | 4 | 2 | 2 | 2 | 3 | 3 | 4 | 3 | 2 | 4 |
| 26 | 1.0   | 2 | 2 | 3 | 0 | 0 | 0 | 2 | 4 | 4 | 3 | 2 | 3 |
| 27 | 1.0   | 2 | 3 | 4 | 3 | 3 | 2 | 3 | 2 | 2 | 0 | 2 | 1 |
| 29 | 1.0   | 4 | 4 | 4 | 3 | 2 | 2 | 4 | 4 | 4 | 4 | 4 | — |
| 32 | 0.25  | 2 | 4 | 4 | 0 | 0 | 1 | 4 | 4 | 4 | 0 | 0 | 4 |
| 33 | 1.0   | 0 | 1 | 4 | 0 | 0 | 0 | 2 | 0 | 3 | 0 | 2 | 4 |
| 46 | 0.25  | 2 | 3 | 4 | 0 | 2 | 2 | 2 | 0 | 3 | 2 | 0 | — |
| 50 | 1.0   | 0 | 4 | 4 | 0 | 0 | 0 | 2 | 3 | 1 | 0 | 0 | 4 |

HERBICIDAL EXAMPLE B (Post-Emergence)

Seeds of the plant species listed below were sown in anodised aluminium pans, 19 cm long×9.5 cm×6 cm deep, containing sterilised sandy loam. They were then watered and placed in a controlled environment room (20° C.; 75-95% relative humidity; 14 hours per day artificial illumination). Fourteen or twenty one days after sowing (depending on the species but when most plants had 2 to 3 true leaves) the seedlings received a foliar spray of the compounds of the Examples listed below, formulated as a solution/suspension in 1:1 by volume of acetone and the wetting agent polyoxyethylene (20 mols) monolaurate solution (2 g per liter).

The concentration of each test compound was calculated to give the desired rate of application of the compound in 450 liters per hectare. After 2 to 3 weeks growth in the controlled environment room the plants were visually assessed for any herbicidal response.

All differences from an untreated control were scored according to an index where 0=no effect, 1=1-24% effect, 2=25-69% effect, 3=70-89% effect and 4=90-100% effect. In the table below, the letters used denote the same plant species as in Herbicidal Example A:

The results obtained were as follows:

| Ex | Kg/ha | a | b | c | d | e | f | g | h | i | j | k | l |
|----|-------|---|---|---|---|---|---|---|---|---|---|---|---|
| 1  | 0.25  | 2 | 3 | 4 | 0 | 0 | 0 | 4 | 3 | 2 | 1 | 0 | — |
| 4  | 0.5   | 1 | 3 | 4 | 0 | 0 | 2 | 3 | 2 | 4 | 0 | 0 | 3 |
| 25 | 1.0   | 3 | 3 | 3 | 2 | 0 | 2 | 4 | 3 | 2 | 3 | 0 | 3 |
| 27 | 1.0   | 3 | 4 | 3 | 2 | 2 | 2 | 3 | 0 | 1 | 2 | 2 | — |
| 29 | 1.0   | 4 | 4 | 4 | 2 | 0 | 0 | 4 | 3 | 2 | 3 | 2 | 4 |
| 32 | 0.25  | 2 | 4 | 4 | 0 | 0 | 0 | 4 | 2 | 3 | 0 | 0 | 4 |
| 42 | 1.0   | 0 | 3 | 4 | 1 | 0 | 0 | 3 | 1 | 3 | 0 | 0 | 0 |
| 50 | 1.0   | 0 | 3 | 2 | 0 | 0 | 0 | 3 | 3 | 1 | 0 | 0 | 4 |
| 60 | 1.0   | 0 | 2 | 2 | 2 | 0 | 0 | 4 | 0 | 3 | 1 | 1 | — |

We claim:

1. A sulphonanilide of the formula:

$$\begin{array}{c} R^2 \\ | \\ NSO_2R^1 \end{array}$$

(I)

and salts thereof, where:

A is nitrogen or a group $CR^5$;
X is oxygen or sulphur;
$R^1$ is an $C_{1-6}$ alkyl, $C_{2-6}$ alkenyl, $C_{2-6}$ alkynyl, $C_{3-7}$ cycloalkyl, phenyl, pyrrolyl, pyridyl, furyl, thienyl, pyrimidinyl, triazolyl, imidazolyl, benzthiophenyl, dihydrogenzofuranyl, thiazolotriazoly, triazolopyrimidinyl or pyrazolopyrimidinyl or amino group;
$R^2$ is hydrogen, $C_{1-6}$ alkyl or $C_{2-5}$ alkanoyl, or a group $-SO_2R^1$;
$R^3$ and $R^4$, which may be the same or different, are each hydrogen, halo, $C_{1-6}$ alkyl, $C_{1-6}$ alkoxy, $C_{3-7}$ cycloalkyl, amino, pyrrolyl, pyrimidinyl, triazolyl, or imidazolyl;
$R^6$, $R^7$ and $R^8$, which may be the same or different, are each hydrogen, halo, cyano, a group $COOR^{10}$, $C_{1-6}$ alkyl, $C_{1-6}$ alkoxy or amino group;
$R^5$ is a group as defined above for $R^6$, $R^7$ and $R^8$, or is pyrimidyloxy or triazinyloxy;
$R^9$ and $R^{10}$ each represent hydrogen of $C_{1-6}$ alkyl group wherein
any alkyl moiety which the groups $R^1$ to $R^{10}$ represent or contain being optionally substituted by one of more halogen atoms, carboxy groups, cyano groups or alkoxycarbonyl groups of 1 to 4 carbon atoms;
any amino group which the groups $R^1$ and $R^3-R^8$ represent being optionally mono- or di-substituted by alkyl of 1 to 4 carbon atoms, alkenyl or 2 to 4 carbon atoms, carbamoyl, or by alkanoyl, alkoxycarbonyl, alkylcarbamoyl or dialkylcarbamoyl in which any alkyl group is of 1 to 4 carbon atoms; and
any phenyl group which group $R^1$ represents being optionally substituted by one or more alkyl, alkoxy carbonyl or alkylthio of 1 to 4 carbon atoms, halogen, cyano, aminosulphonyl or nitro.

2. A compound according to claim 1 in which $R^1$ represents methyl, ethyl, n-propyl, isopropyl, n-butyl, t-butyl, chloromethyl, flouromethyl, cyanomethyl, carboxymethyl, trifluoromethyl, methoxycarbonylmethyl, ethoxycarbonylmethyl, vinyl, allyl, propargyl, cyclopentyl, cyclohexyl, phenyl (substituted by chlorine, bromine, fluorine, methyl, methoxy, trifluoromethyl, methylthio, methoxycarbonyl, ethoxycarbonyl or nitro), pyrrolyl, pyridyl, furyl, 2-thienyl, pyrimidinyl, 1-triazolyl, 1-imidazolyl, thiazolotriazolyl, triazolopyrimidinyl, pyrazolopyrimidinyl, benzthiophenyl, benzodioxolyl, quinolinyl, quinazolinyl, benzothiazolyl or dihydrobenzofuranyl.

3. A compound according to claim 1 in which $R^2$ represents hydrogen.

4. A compound according to claim 1 in which $R^3$ and $R^4$ each represent hydrogen, methyl, methoxy or chloro.

5. A compound according to claim 1 in which A represents a group $CR^5$ where $R^5$ represents hydrogen, fluoro, chloro, bromo, methyl or trifluoromethyl.

6. A compound according to claim 1 in which $R^6$, $R^7$ and $R^8$ each represent hydrogen, methyl or chloro.

7. 2'-Chloro-6'-(4,6-dimethoxy-2-pyrimidinyloxy)-1,1,1-trifluoromethanesulphonanilide.

8. A compound according to claim 1 in which A is $CR^5$; Y is $CR^9$; $R^2$, $R^6$, $R^7$, $R^8$ and $R^9$ are hydrogen; and $R^3$ and $R^4$ are methoxy.

9. A compound according to claim 8 in which $R^1$ is thiazolotriazolyl, methyl, cyanomethyl or trifluoromethyl.

10. A herbicidal composition which comprises an effective herbicidal amount of at least one compound according to claim 1 in combination with a carrier therefor.

11. A herbicidal composition which comprises an effective herbicidal amount of at least one compound according to claim 2 in combination with a carrier therefor.

12. A herbicidal composition which comprises an effective herbicidal amount of at least one compound according to claim 7 in combination with a carrier therefor.

13. A herbicidal composition which comprises an effective herbicidal amount of at least one compound according to claim 8 in combination with a carrier therefor.

14. A method of combating weeds which comprises applying to a locus infested or liable to infestation therewith and effective amount of at least one compound according to claim 1.

15. A method of combating weeds which comprises applying to a locus infested or liable to infestation therewith and effective amount of at least one compound according to claim 2.

16. A method of combating weeds which comprises applying to a locus infested or liable to infestation therewith and effective amount of at least one compound according to claim 7.

17. A method of combating weeds which comprises applying to a locus infested or liable to infestation therewith an effective amount of at least one compound according to claim 8.

18. A compound according to claim 9 in which $R^5$ is F or Cl, X is O, $R^1$ is trifluoromethyl or cyanomethyl.

19. A herbicidal composition which comprises an effective herbicidal amount or at least one compound according to claim 18 in combination with a carrier therefor.

20. A method of combating weeds which comprises applying to a locus infested of liable to infestation therewith an effective amount of at least one compound according to claim 18.

* * * * *